(12) United States Patent
Czaplewski et al.

(10) Patent No.: US 10,391,226 B2
(45) Date of Patent: Aug. 27, 2019

(54) AIR BUBBLE REMOVAL FROM EXTRACORPOREAL BLOOD VIA CHEMICAL ENTRAPMENT OF NITROGEN

(71) Applicant: International Business Machines Corporation, Armonk, NY (US)

(72) Inventors: Sarah K. Czaplewski, Rochester, MN (US); Joseph Kuczynski, North Port, FL (US); Jason T. Wertz, Pleasant Valley, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 152 days.

(21) Appl. No.: 15/426,549

(22) Filed: Feb. 7, 2017

(65) Prior Publication Data

US 2018/0221558 A1 Aug. 9, 2018

(51) Int. Cl.
| | | |
|---|---|---|
| *B01D 19/00* | (2006.01) | |
| *A61M 1/36* | (2006.01) | |
| *B01J 20/22* | (2006.01) | |
| *B01J 20/28* | (2006.01) | |

(52) U.S. Cl.
CPC ........ *A61M 1/3627* (2013.01); *B01D 19/0005* (2013.01); *B01D 19/0031* (2013.01); *B01J 20/223* (2013.01); *B01J 20/28059* (2013.01); *A61M 1/3679* (2013.01); *A61M 2202/0266* (2013.01)

(58) Field of Classification Search
CPC .............................................................. B01D 19/00–0495; A61M 2005/3123; A61M 5/36–40; A61M 1/36–387; B01J 20/22–268
USPC .................................. 95/130; 604/122–127
See application file for complete search history.

(56) References Cited

U.S. PATENT DOCUMENTS

| | | |
|---|---|---|
| 4,568,327 A | 2/1986 | Seufert |
| 4,572,724 A | 2/1986 | Rosenberg et al. |
| 5,695,717 A | 12/1997 | Polaschegg et al. |
| 5,922,317 A | 7/1999 | Kayar et al. |
| 5,997,816 A | 12/1999 | McIntosh et al. |
| 7,699,799 B2 | 4/2010 | Blanton |
| 8,444,586 B2 | 5/2013 | Beck |
| 8,894,749 B2 | 11/2014 | Jonsson et al. |
| 8,979,788 B2 | 3/2015 | Demers et al. |
| 2003/0026730 A1* | 2/2003 | Sevastianov ........ A61M 1/3627 422/44 |
| 2005/0192525 A1 | 9/2005 | Wieting et al. |

OTHER PUBLICATIONS

Berman et al., *Removal of Gas Micro Emboli From Extracorporeal Circulation and Intravenous Fluid Systems*, Proceedings, AAMI 19th Annual Meeting, Abstracts on the Application of Technology to Health Care, Apr. 1984, Washington, D.C.

(Continued)

*Primary Examiner* — T. Bennett McKenzie
(74) *Attorney, Agent, or Firm* — Robert J. Shatto

(57) ABSTRACT

A process includes removing air bubbles from extracorporeal blood via chemical entrapment of nitrogen ($N_2$) gas.

5 Claims, 3 Drawing Sheets

(56) References Cited

OTHER PUBLICATIONS

Mino et al., *Ultrasound bubble filter using the flexural vibration of a cylinder for an extracorporeal circulation circuit*, Sensors and Actuators A: Physical, vol. 199, dated Sep. 1, 2013, pp. 202-208, ScienceDirect.com, Elsevier B.V., Amsterdam.

Keshavarzi et al., *Effectiveness of microbubble removal in an airtrap with a free surface interface*, Journal of Biomechanics, vol. 48, Issue 7, May 2015, pp. 1237-1240, Elsevier Inc., Amsterdam.

Schwarz et al., *The acoustic filter: an ultrasonic blood filter for the heart-lung machine*, Journal of Thoracic and Cardiovascular Surgery, vol. 104, Issue 6, pp. 1647-1653, Dec. 1992, Mosby-Year Book, Inc., St. Louis, MO.

Baumann et al., *Synthesis of High-Surface-Area Alumina Aerogels without the Use of Alkoxide Precursors*, Chemistry and Material Science Directorate and Energy and Environment Directorate, Lawrence Livermore National Laboratory, 17(2), American Chemical Society, Publication Date (Web): Dec. 24, 2004, 7 pages.

Bustanafruz et al., *Specific Surface Area Increment of Alumina Nanoparticles Using Mineral Fuels in Combustion Synthesis*, Journal of Nanostructures, published online Jan. 6, 20125, 7 pages.

Karim et al., *Synthesis of γ-Alumina Particles and Surface Characterization*, The Open Colloid Science Journal, vol. 4, Accepted: May 3, 2011, 5 pages.

Pugsley et al., *The impact of microemboli during cardiopulmonary bypass in neuropsychological functioning*, 25(7), dated Jul. 1994, Abstract Only, 1 page, PubMed.gov (online), URL: www.ncbi.nlm.nih.gov/pubmed/8023354.

Maksimowski et al., *Nitrogen fixation on supported titanium complexes*, Journal of Molecular Catalysis, 68(3), Apr. 1991, pp. 371-378, Elsevier Sequoia, Lausanne, The Netherlands.

Clark et al., *Mircoemboli during coronary artery bypass grafting. Genesis and effect on outcome*, Journal of Thoracic and Cardiovascular Surgery, 109(2), dated Feb. 1995, Abstract Only, 1 page, PubMed.gov (online), URL: www.ncbi.nlm.nih.gov/pubmed/7853878.

Roach et al., *Adverse Cerebral Outcomes after Coronary Bypass Surgery*, The New England Journal of Medicine, vol. 335, Massachusetts Medical Society, downloaded from: http://scholarscompass.vcu.edu/anesth_pubs/3, date of submission: Jan. 2015, 9 pages.

Walzer et al., *Neuropsychological disorders after coronary bypass surgery*, Journal of Neurology and Psychiatry, vol. 62, published by group.bmj.com, downloaded from http://jnnp.bmj.com/ on Oct. 11, 2016, 6 pages.

Zaki et al., *Using modified Pechini method to synthesize α-Al2O3 nanoparticles of high surface area*, Ceramics International, vol. 38, Issue 6, dated Aug. 2012, 6 pages.

Schonburg et al., *Significant reduction of air microbubbles with the dynamic bubble trap during cardiopulmonary bypass*, Presented at the Annual Seminar if the American Academy of Cardiovascular Perfusion, vol. 16, dated Jan. 2000, 8 pages.

Perthel et al., *Use of a dynamic bubble trap in the arterial line reduces microbubbles during cardiopulmonary bypass and microembolic signals in the middle cerebral artery*, Presented at the Annual Seminar of the American Academy of Cardiovascular Perfusion, vol. 20, dated Jan. 2004, 7 pages.

Innocentive, *Microbubble Removal from Extracorporeal Bloodstream*, InnoCentive, Inc. <https://www.innocentive.com/ar/challenge/9933816>, printed Jan. 11, 2017, 2 pages.

\* cited by examiner

AIR BUBBLE REMOVAL FROM EXTRACORPOREAL BLOOD VIA CHEMICAL ENTRAPMENT OF NITROGEN

BACKGROUND

Various medical treatments and procedures require a patient's blood to be circulated outside the body (also referred to as an "extracorporeal bloodstream"). Micro-leaks in bloodstream circulation equipment and degassing effects from the blood may cause air bubbles to build up in the extracorporeal bloodstream during medical treatments. Re-insertion of such air bubbles into the patient can lead to fatal embolisms. To illustrate, cerebral microemboli generated during a cardiopulmonary bypass procedure may result in neurological impairment that is a major cause of morbidity and mortality after open heart surgery.

There have been numerous attempts to remove microbubbles from extracorporeal blood. While it is possible to remove larger air bubbles before the blood is re-inserted into the patient, there are challenges associated with the removal of smaller air bubbles (also referred to as "microbubbles" having a diameter in a size range of about 2.5 μm to 50 μm). Current solutions may enable partial mitigation of the air bubble removal problem (e.g., drip chambers) or may require undesired changes and interruptions in the treatments (e.g., reducing the bloodflow). Accordingly, there is a need for new techniques to efficiently and continuously remove microbubbles from extracorporeal bloodstreams in order to reduce the risk of microemboli.

SUMMARY

According to an embodiment, a process comprises removing air bubbles from extracorporeal blood via chemical entrapment of nitrogen ($N_2$) gas.

According to another embodiment, an extracorporeal blood treatment system is disclosed. The system includes an air bubble removal component to remove air bubbles from extracorporeal blood via chemical entrapment of nitrogen ($N_2$) gas.

According to another embodiment, an article of manufacture includes an organometallic complex bound to a surface of a particle. The organometallic complex is utilized to remove air bubbles from extracorporeal blood via chemical entrapment of nitrogen ($N_2$) gas by dinitrogen fixation.

The foregoing and other objects, features, and advantages of the invention will be apparent from the following more particular descriptions of exemplary embodiments of the invention as illustrated in the accompanying drawings wherein like reference numbers generally represent like parts of exemplary embodiments of the invention.

DETAILED DESCRIPTION

The present disclosure describes systems and methods of nitrogen gas removal from extracorporeal blood via chemical entrapment. Nitrogen gas ($N_2$) represents the majority of the content (about 78 percent) of air bubbles that may be formed in extracorporeal blood as a result of micro-leaks in bloodstream circulation equipment and degassing effects from the blood. In the present disclosure, the nitrogen gas in the air bubbles may be "fixed" via a reaction with a suitable organometallic compound or a nitrogenase. As nitrogen gas represents the majority of the air bubble content, complexation of nitrogen may result in collapse of the air bubbles (including microbubbles). Accordingly, the systems and methods of chemical entrapment of nitrogen gas described herein may enable efficient and continuous removal of microbubbles from an extracorporeal bloodstream in order to reduce the risk of microemboli.

Figure 1:
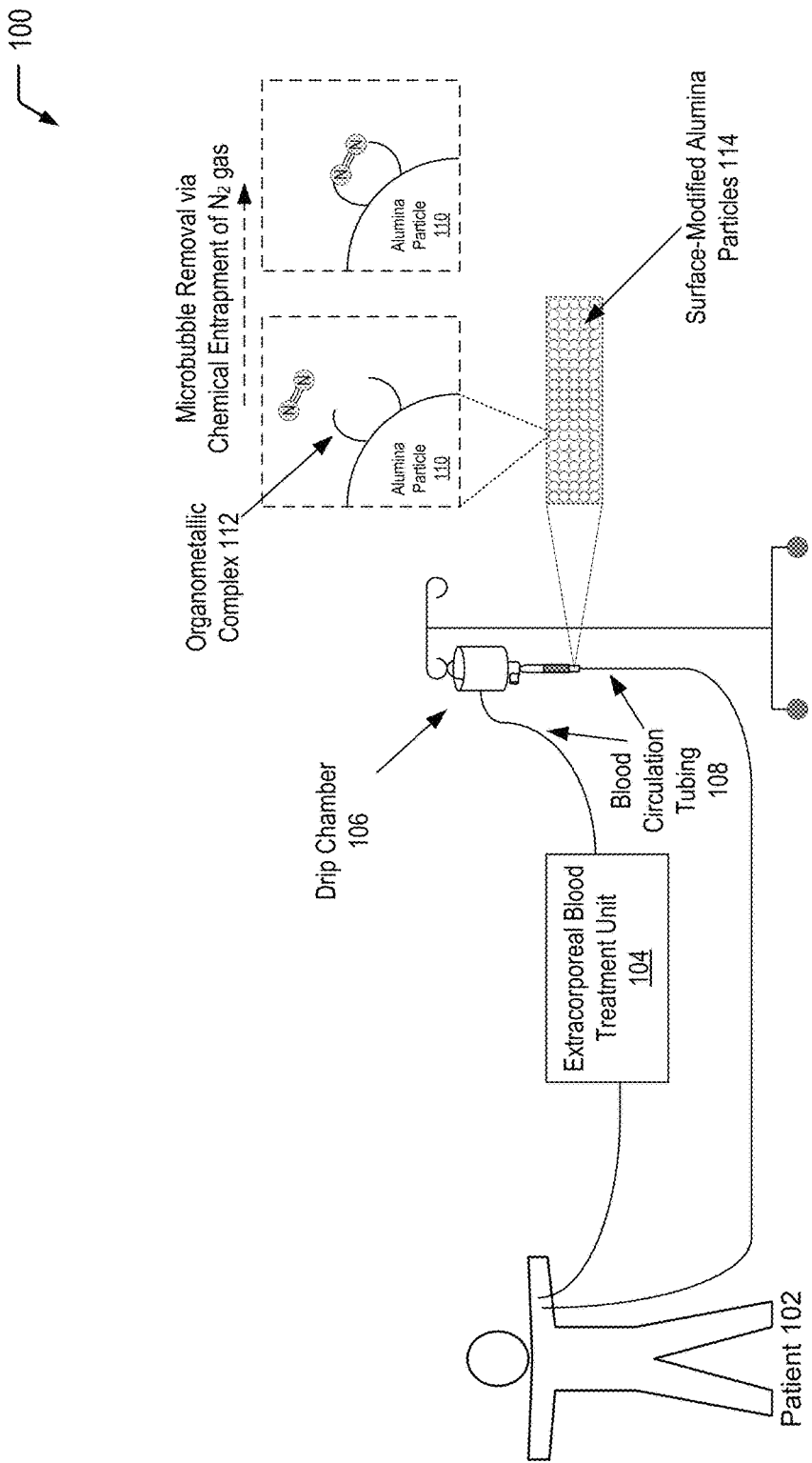
FIG. 1 is a diagram of an extracorporeal blood treatment system to remove air bubbles from extracorporeal blood via chemical entrapment of nitrogen gas, according to one embodiment.

Referring to FIG. 1, a diagram 100 illustrates an extracorporeal blood treatment system for nitrogen gas removal from extracorporeal blood via chemical entrapment, according to one embodiment. As described further herein, the extracorporeal blood treatment system of FIG. 1 may enable efficient and continuous removal of microbubbles from an extracorporeal bloodstream in order to reduce the risk of microemboli.

FIG. 1 illustrates an example of a medical treatment in which the blood of a patient 102 is circulated outside of the patient's body for treatment using an extracorporeal blood treatment unit 104. For ease of illustration purposes, FIG. 1 depicts the extracorporeal blood treatment unit 104 as a single unit. However, it will be appreciated that alternative numbers and/or types of extracorporeal bloodstream circulation equipment may be utilized depending on the particular medical treatment. As an illustrative, non-limiting example, for a cardiopulmonary bypass procedure, the patient 102 may require extracorporeal bloodstream treatment during the procedure, after the procedure, or both. One challenge associated with such an extracorporeal bloodstream treatment is that micro-leaks in the bloodstream circulation equipment and/or degassing effects from the blood may cause air bubbles to build up in the extracorporeal bloodstream. Re-insertion of such air bubbles into the patient 102 can lead to fatal embolisms. Accordingly, it is important to reduce or eliminate air bubbles from the treated blood prior to re-insertion of the blood into the patient 102 in order to reduce the risk of neurological impairment to the patient 102. FIG. 1 illustrates that a drip chamber 106 (coupled to blood circulation tubing 108) may enable partial mitigation of the air bubble removal problem. As previously described herein, the drip chamber 106 may enable removal of larger air bubbles, but removal of microbubbles remains a challenge.

FIG. 1 illustrates an example of an extracorporeal blood treatment system in which an alumina particle 110 having an organometallic complex 112 (e.g., a titanium complex) bound to a surface of the alumina particle 110 (identified as "Surface-Modified Alumina Particles" 114 in FIG. 1) may enable removal of microbubbles from extracorporeal blood via chemical entrapment of nitrogen ($N_2$) gas by dinitrogen fixation. As nitrogen gas represents the majority of the air bubble content, complexation of nitrogen using the surface-modified alumina particles 114 may result in collapse of the air bubbles (including microbubbles), thereby preventing the re-introduction of such air bubbles into the patient 102.

In other embodiments, other types of particles may be utilized, such as silica or magnesia, among other alternatives. Further, various organometallic complexes have been demonstrated to sequester atmospheric nitrogen. Of the several organometallic complexes known to bind dinitrogen, titanium complexes supported on alumina have been demonstrated to result in the most effective dinitrogen fixation yield. Accordingly, while the present disclosure describes an example of a titanium complex bound to an alumina particle, it will be appreciated that alternative and/or additional types of particles and organometallic complexes may be utilized for microbubble removal from an extracorporeal bloodstream.

Figure 2:
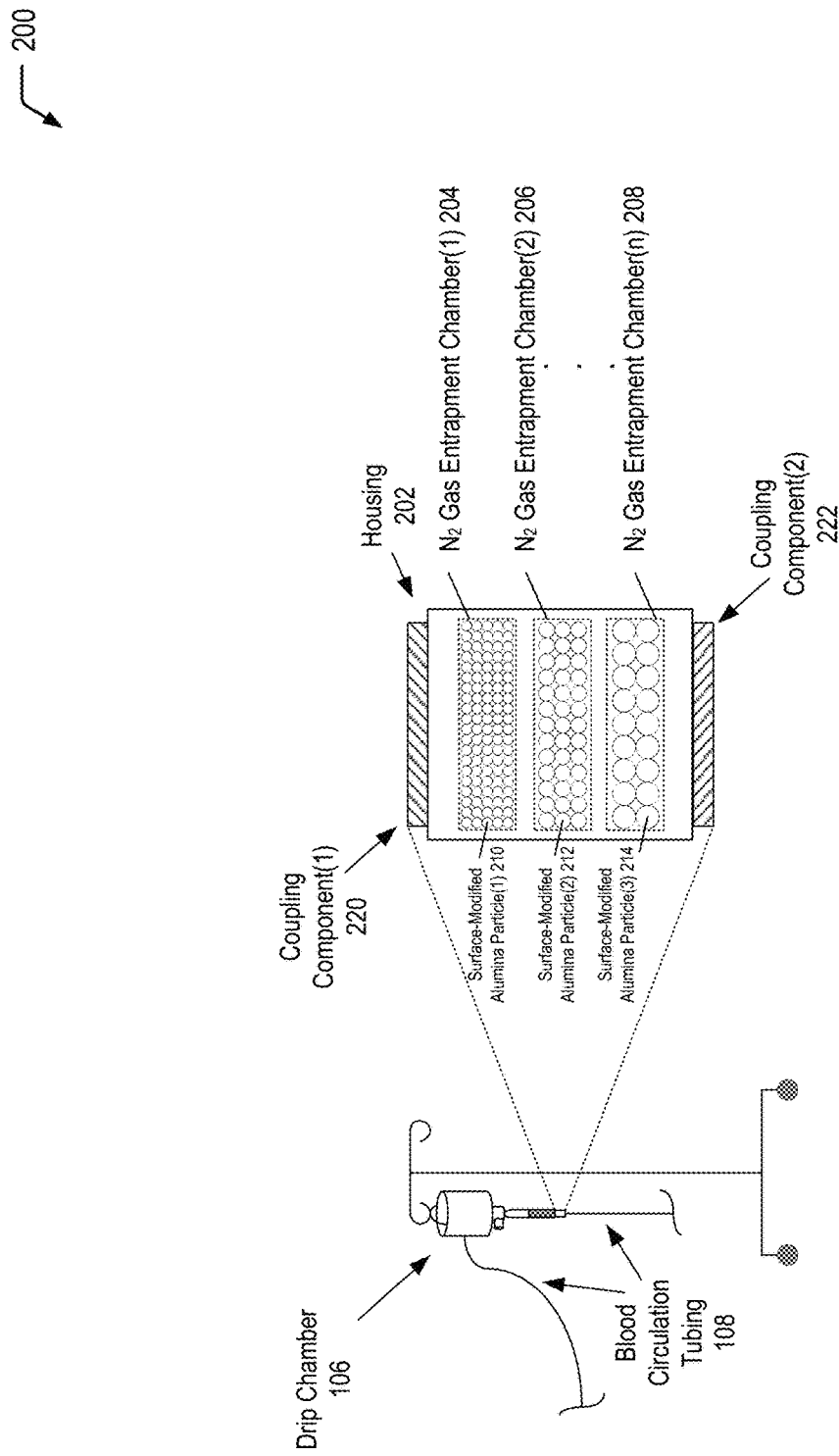
FIG. 2 is a diagram illustrating a particular embodiment of an extracorporeal blood treatment system that includes an air bubble removal component having multiple chambers of different surface-modified particles, representing a multiple-stage approach to chemical entrapment of nitrogen gas.

While FIG. 1 illustrates an example of an extracorporeal blood treatment system that includes an air bubble removal component (incorporated within or downstream of the drip chamber 106) that has a single set of surface-modified alumina particles 114 (e.g., high surface area nanoparticles having a particle size in a range of about 100 nm to 200 nm), it will be appreciated that multiple types and/or arrangements of particles may be utilized for microbubble removal. For example, as illustrated and further described herein with respect to FIG. 2, the extracorporeal blood treatment system of the present disclosure may include an air bubble removal component that utilizes multiple sets of surface-modified particles in different size ranges (with corresponding differences in surface area available for dinitrogen fixation). FIG. 2 depicts one example of such an approach in which multiple particle "chambers" are arranged in series (with respect to the direction of blood flow within the blood circulation tubing 108), with each chamber associated with a different "stage" in a multiple-stage process of chemical entrapment of nitrogen. Such a multiple-stage approach may improve the efficiency of nitrogen gas removal via chemical entrapment. It will be appreciated that the multiple-stage approach depicted in FIG. 2 is an illustrative, non-limiting example and that alternative numbers and/or arrangements of chambers, particles, etc. may be used in order to improve nitrogen fixation efficiency.

The surface-modified alumina particles 114 may be incorporated into various types of manufactured articles. For example, the surface-modified alumina particles 114 may correspond to a powder that is packed into a base of the drip chamber 106 where the extracorporeal blood is permitted to flow after treatment by the extracorporeal blood treatment unit 104. Alternatively, while not shown in the example of FIG. 1, the surface-modified alumina particles 114 may be incorporated into a separate microbubble removal chamber that may be downstream of the drip chamber 106 prior to re-introduction of the treated blood into the patient 102.

In some cases, the surface-modified alumina particles 114 may be incorporated into the drip chamber 106 during manufacturing of the drip chamber 106. In other cases, the drip chamber 106 may correspond to a conventional drip chamber, and the surface-modified alumina particles 114 may be incorporated into a separate article of manufacture that may be connected to the drip chamber 106 or otherwise positioned downstream of the drip chamber 106 in the extracorporeal blood stream. Thus, in some cases, a manufacturer of the drip chamber 106 may incorporate the surface-modified alumina particles 114 into the drip chamber 106. In other cases, the surface-modified alumina particles 114 may be disposed within a housing (such as the housing 202 depicted in FIG. 2) that may include one or more coupling components to enable the housing to be positioned downstream of the drip chamber 106. To illustrate, the housing may include a male/female coupling component for attachment of the housing to a corresponding male/female coupling component of the drip chamber 106. The housing may also include another coupling component for insertion of the blood circulation tubing 108. It will be appreciated that the surface-modified alumina particles 114 may be incorporated into various alternative and/or additional manufactured articles to enable microbubble removal from an extracorporeal bloodstream prior to re-insertion into the patient 102.

In a particular embodiment, the surface-modified alumina particles 114 of FIG. 1 may include nanoparticulate alumina, such as a powder having a high surface area (e.g., in a range between 60 $m^2/g$ and 70 $m^2/g$). Corundum ($\alpha$-$Al_2O_3$) has significant importance in the field of catalytic applications because it exists in a thermodynamically stable phase at standard pressure and temperature conditions. However, its very low surface area represents a serious drawback. The "Pechini" method belongs to the sol-gel category of fabrication methods. In this method, an $\alpha$-hydroxycarboxylic-containing compound forms a polybasic acid chelate with metal cations which successively polymerize with a polyhydroxy alcohol. After a calcination process, nanometer-sized powders may be achieved. Compared to other sol-gel methods, the Pechini method has better compositional homogeneity, lower toxicity and lower cost. In a particular embodiment of the present disclosure, a modified water-based Pechini method may be utilized to prepare $\alpha$-alumina nanoparticles that are highly crystalline and have a high specific surface area (e.g., a Brunauer-Emmett-Teller (BET) surface area from 18 $m^2/g$ to 66 $m^2/g$, or more) at a relatively low calcination temperature of about 900° C. To illustrate, alumina powders with a high specific surface area may be prepared using a polymerizing-chelating synthesis process. An example of such a polymerizing-chelating synthesis process includes a polymer preparation stage, followed by an alumina preparation stage.

As an illustrative, non-limiting example, the polymer preparation stage may include mixing 0.12 mole of anhydrous citric acid with 0.1 mole of anhydrous acrylic acid in the presence of 0.1% hydroquinone. The blend temperature may be increased gradually to 120-170° C. Esterification may occur at about 120° C., and the polymerization may be carried out at higher temperatures to obtain a high viscosity polymer with a white-yellowish color. The alumina preparation stage may include heating 10 g of the previously prepared viscous polymer to 80° C. with stirring. The polymerizing-chelating, drying, and successive pyrolysis processes may be performed using techniques known to one of ordinary skill in the art.

For example, the required volume of an aluminum nitrate nonahydrate solution with a desired concentration may be added to the polyester, and stirring may continue for about another hour. The solutions may then be slowly heated to 140° C. and maintained at this temperature until removal of water is nearly complete (about 2.5 hours). The resulting clear gel may be transferred to an electrical furnace and dried at 150° C. overnight, yielding a solid resin of high porosity. The resulting resin may be ground in an agate mortar and subjected to a pyrolysis process at 450° C. (heating rate 5° C./minute) for 4 hours in glazed alumina crucibles. Subsequently, the pyrolysis product may be subjected to a calcination process at 900° C. (heating rate 5° C./minute) in the presence of purified air.

In a particular embodiment, the organometallic complex 112 may include a titanium complex to sequester nitrogen gas from an air microbubble via a complexation reaction that binds dinitrogen to the surface of the alumina particle 110. In a particular embodiment, the supported complex may be prepared by reaction of a trichloro-cyclopentadienyl titanium compound (CpTiCl$_3$) with the surface hydroxyl groups of the alumina particle 110. The bound titanium (IV) complex is formally electron deficient, rendering it susceptible to attack by the lone electron pair of dinitrogen.

As an illustrative, non-limiting example, the surface-modified alumina particles 114 depicted in FIG. 1 may be formed in two steps. In the first step, CpTiCl$_3$ may react with surface hydroxyl groups, leading to formation of Ti(IV) surface-bonded complexes and HCl (as depicted in the chemical reaction diagram shown in step 304 of FIG. 3). In the second step, the Ti(IV) surface complexes may be reduced with a reducing agent. An illustrative, non-limiting example of a reducing agent includes an alkali metal naphthalene. To illustrate, reduction may include the use of sodium naphthalene (NaNp) or lithium naphthalene (LiNp) in a nitrogen atmosphere. In a particular embodiment, the bound titanium complex may first be reduced with NaNp in a ratio exceeding 10:1, which may result in a first dinitrogen fixation yield. When the titanium surface complex is first reduced with NaNp (e.g., at room temperature for 2 hours), washed, and dried, the dinitrogen fixation yield may increase to a second dinitrogen fixation yield that is greater than the first dinitrogen fixation yield.

Thus, FIG. 1 illustrates an example of an extracorporeal blood treatment system for nitrogen gas removal from extracorporeal blood via chemical entrapment. The extracorporeal blood treatment system of FIG. 1 may enable efficient and continuous removal of microbubbles from an extracorporeal bloodstream in order to reduce the risk of microemboli.

FIG. 2 is a diagram 200 that illustrates selected portions of the extracorporeal blood treatment system depicted in FIG. 1 and that illustrates a multiple-stage approach to chemical entrapment of nitrogen gas using multiple particulate chambers, according to one embodiment.

In the multiple-stage approach depicted in FIG. 2, the air removal component of the extracorporeal blood treatment system includes multiple nitrogen gas entrapment chambers disposed within a housing 202. FIG. 2 illustrates that at least a first nitrogen gas entrapment chamber 204 (identified as "N$_2$ Gas Entrapment Chamber(1)" in FIG. 2) and a second nitrogen gas entrapment chamber 206 (identified as "N$_2$ Gas Entrapment Chamber(2)" in FIG. 2) are disposed within the housing 202. FIG. 2 further illustrates that, in some cases, more than two nitrogen gas entrapment chambers may be disposed within the housing 202, with the (optional) additional nitrogen gas entrapment chamber(s) 208 represented by the integer n. In a particular embodiment, the additional nitrogen gas entrapment chamber(s) 208 may correspond to a single additional nitrogen gas entrapment chamber (i.e., n=3), representing a three-stage approach to chemical entrapment of nitrogen gas.

FIG. 2 illustrates that the first nitrogen gas entrapment chamber 204 may contain a first set of surface-modified alumina particles 210 (with one of the particles identified as "Surface-Modified Alumina Particle(1)" in FIG. 2). The second nitrogen gas entrapment chamber 206 may contain a second set of surface-modified alumina particles 212 (with one of the particles identified as "Surface-Modified Alumina Particle(2)" in FIG. 2). In the particular embodiment depicted in FIG. 2, where the multiple-stage approach includes at least three nitrogen gas entrapment chambers, the at least one additional nitrogen gas entrapment chamber 208 includes a third set of surface-modified alumina particles 214 (with one of the particles identified as "Surface-Modified Alumina Particle(3)" in FIG. 2).

FIG. 2 illustrates that the different sets of particles disposed within the nitrogen gas entrapment chambers 204-208 may have different particle size ranges and/or surface areas. For example, the first set of surface-modified alumina particles 210 may include alumina nanoparticles having an average particle size in a first particle size range, the second set of surface-modified alumina particles 212 may include alumina nanoparticles having an average particle size in a second particle size range, and the third set of surface-modified alumina particles 214 may include alumina nanoparticles having an average particle size in a third particle size range.

In the particular embodiment depicted in FIG. 2, the air bubble removal component of the extracorporeal blood treatment system corresponds to an article of manufacture that includes at least the housing 202, and the housing 202 is separate from the drip chamber 106. In alternative embodiments, the chemical entrapment components depicted within the housing 202 may be "packed" into or otherwise disposed within a base of the drip chamber 106. FIG. 2 illustrates that, in cases where the housing 202 is a separate article of manufacture from the drip chamber 106, the housing 202 may include a first coupling component 220 (identified as "Coupling Component(1)" in FIG. 2) to enable attachment of the housing 202 to the drip chamber 106. FIG. 2 illustrates that the housing 202 may further include a second coupling component 222 (identified as "Coupling Component(2)" in FIG. 2) to enable insertion of the blood circulation tubing 108.

FIG. 2 depicts an illustrative, non-limiting example in which the first set of surface-modified alumina particles 210 disposed within the first nitrogen gas entrapment chamber 204 corresponds to the first stage of chemical entrapment of nitrogen gas in air bubbles that may flow into the housing 202 from the drip chamber 106. Accordingly, the first set of surface-modified alumina particles 210 encounters the highest concentration of nitrogen gas in the bubbles (e.g., about 78 percent). As a result of nitrogen fixation in the first nitrogen gas entrapment chamber 204, the second set of surface-modified alumina particles 212 in the second nitrogen gas entrapment chamber 206 encounters a lower concentration of nitrogen gas in the bubbles (in cases where all bubbles have not collapsed during the first stage). Nitrogen fixation in the second nitrogen gas entrapment chamber 206 further reduces the concentration of nitrogen gas. In the example of FIG. 2, where there is at least one additional nitrogen gas entrapment chamber 208, the third set of surface-modified alumina particles 214 in the additional nitrogen gas entrapment chamber(s) 208 encounters a still lower concentration of nitrogen gas in any remaining bubbles that have not collapsed during the second stage.

As such, for improved nitrogen fixation efficiency, it may be desirable to utilize relatively small nanoparticles (also referred to herein as "high surface area" particles) as the first set of surface-modified alumina particles 210 in the first nitrogen gas entrapment chamber 204 for the first stage of the multiple-stage chemical entrapment of nitrogen gas. As a result of the reduction in the nitrogen gas concentration in bubbles that have not collapsed prior to exiting the first nitrogen gas entrapment chamber 204, it may be possible to utilize larger nanoparticles (also referred to herein as "medium surface area" particles) as the second set of surface-modified alumina particles 212. As a result of the further reduction in the nitrogen gas concentration in bubbles that have not collapsed prior to exiting the second nitrogen gas entrapment chamber 206, it may be possible to utilize still larger nanoparticles (also referred to herein as "low surface area" particles) in the subsequent nitrogen gas entrapment chamber(s) 208. It will be appreciated that numerous other alternative sequences and/or arrangements may also be utilized. One example of an alternative three-stage approach may include utilizing relatively high surface area particles, followed by relatively low surface area particles, followed by relatively high surface area particles.

Thus, in some embodiments, the first set of surface-modified alumina particles 210 may have a first average particle size, and the second set of surface-modified alumina particles 212 may have a second average particle size that is greater than the first average particle size. Further, in cases where more than two nitrogen gas entrapment chambers are utilized, the third set of surface-modified alumina particles 214 may have a third average particle size that is greater than the second average particle size. As illustrative, non-limiting examples, the first average particle size may be in a range of 100 nm to 200 nm, the second average particle size may be in a range of 400 nm to 500 nm, and the third average particle size may be in a range of 800 nm to 1000 nm. One of ordinary skill in the art will appreciate that various particle size ranges or combinations of particle size ranges that are sufficient to cause microbubble collapse due to chemical entrapment of nitrogen may be empirically determined.

Figure 3:
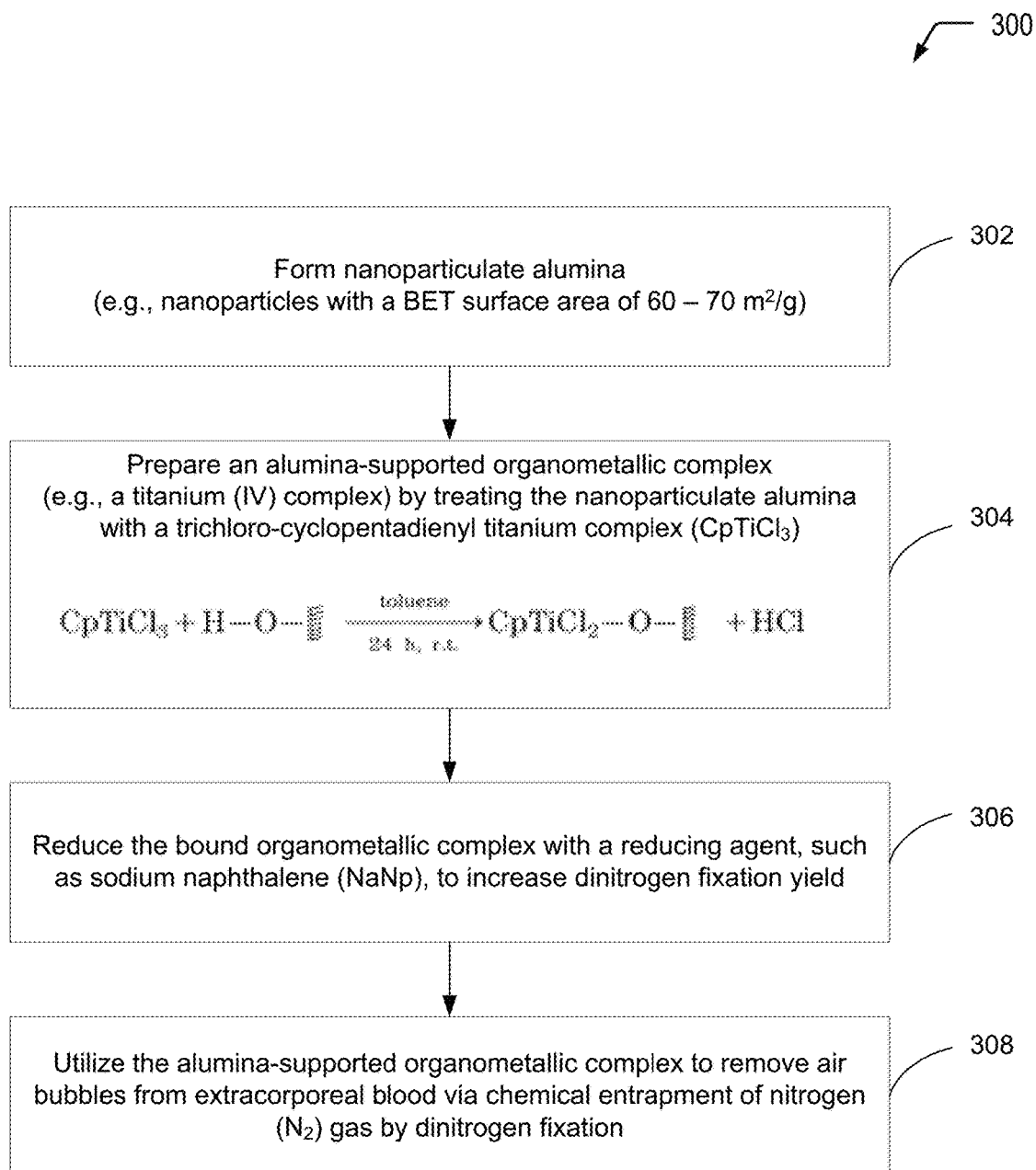
FIG. 3 is a flow diagram illustrating a particular embodiment of a process of removing air bubbles from extracorporeal blood via chemical entrapment of nitrogen gas.

Referring to FIG. 3, a flow diagram illustrates an example of a process 300 of removing air bubbles from extracorporeal blood via chemical entrapment of nitrogen gas, according to one embodiment. In the particular embodiment illustrated in FIG. 3, the process 300 includes forming an alumina-supported organometallic complex and utilizing the alumina-supported organometallic complex to remove air bubbles from extracorporeal blood via chemical entrapment of nitrogen gas. It will be appreciated that the operations shown in FIG. 3 are for illustrative purposes only and that the operations may be performed in alternative orders, at alternative times, by a single entity or by multiple entities, or a combination thereof. As an example, one entity may form alumina nanoparticles having an average particle size in desired particle size range(s), while another entity may form the alumina-supported organometallic complex (including reduction of the bound titanium complex for increased dinitrogen fixation yield), and another entity may form an article of manufacture that includes the alumina-supported organometallic complex (e.g., a modified drip chamber or a component of a drip chamber). Further, yet another entity may utilize the article of manufacture that includes the alumina-supported organometallic complex for removal of air bubbles (e.g., microbubbles) from extracorporeal blood via nitrogen sequestration.

The process 300 includes forming nanoparticulate alumina, at 302. For example, a modified water-based Pechini method may be utilized to prepare α-alumina nanoparticles that are highly crystalline and have a high specific surface area (as previously described herein with respect to FIG. 1). As an example, referring to FIG. 1, forming the nanoparticulate alumina may include forming the surface-modified alumina particles 114. As another example, in the case of a multiple-stage approach such as the approach described with respect to FIG. 2, forming the nanoparticulate alumina may include forming a first set of alumina nanoparticles of a first size (e.g., the first set of surface-modified alumina particles 210 depicted in the first nitrogen gas entrapment chamber 204) and forming a second set of alumina nanoparticles of a second size (e.g., the second set of surface-modified alumina particles 212 depicted in the second nitrogen gas entrapment chamber 206). In a multiple-stage approach that includes at least one additional nitrogen gas entrapment chamber (e.g., the third nitrogen gas entrapment chamber 208 of FIG. 2), the process 300 may further include forming one or more additional sets of alumina nanoparticles (e.g., the third set of surface-modified alumina particles 214 depicted in the third nitrogen gas entrapment chamber 208 of FIG. 2).

The process 300 includes preparing an alumina-supported organometallic complex by treating the nanoparticulate alumina, at 304. For example, the organometallic complex may include a titanium (IV) complex. In this case, the nanoparticulate alumina may be treated with a trichloro-cyclopentadienyl titanium complex ($CpTiCl_3$), as previously described herein with respect to FIG. 1.

The process 300 also includes reducing the bound organometallic complex with a reducing agent to increase dinitrogen fixation yield, at 306. To illustrate, in the case of a titanium complex, the surface titanium complex may be reduced with an alkali metal naphthalene (e.g., NaNp, LiNp, etc.) in a nitrogen atmosphere, as previously described herein with respect to FIG. 1.

The process 300 further includes utilizing the alumina-supported organometallic complex to remove air bubbles from extracorporeal blood via chemical entrapment of nitrogen gas by dinitrogen fixation, at 308. For example, the surface-modified alumina particles 114 depicted in FIG. 1 may be utilized for microbubble removal via chemical entrapment of $N_2$ gas. As another example, in a multiple-stage approach such as the approach depicted in FIG. 2, multiple sets of surface-modified alumina particles may be utilized. For example, referring to FIG. 2, the first set of surface-modified alumina particles 210 disposed within the first nitrogen gas entrapment chamber 204 may be utilized for a first stage of microbubble removal via chemical entrapment of $N_2$ gas, the second set of surface-modified alumina particles 212 may be utilized for a second stage of microbubble removal, and the third set of surface-modified alumina particles 214 may be utilized for a third stage of microbubble removal.

Thus, FIG. 3 illustrates an example of a process of removing air bubbles from extracorporeal blood via chemical entrapment of nitrogen gas using an organometallic complex bound to a surface of an alumina particle. As described further herein, the organometallic complex may be bound to nanoparticulate alumina that is treated to increase the number of reactive sites on the surface of the alumina, thereby increasing the ability of the active complex to bind dinitrogen. In some cases, the alumina-supported organometallic complex, in the form of a powder, may be packed into the base of a drip chamber into which the extracorporeal blood is permitted to flow (as depicted in the embodiment of FIG. 1). As an alternative to a modified drip chamber, a separate microbubble removal chamber that includes the alumina-supported organometallic complex may be utilized. The high surface area and number of active nitrogen fixation sites of the nanoparticulate alumina powder may reduce the time required to sequester dinitrogen from the air microbubbles. Once nitrogen has been bound to the particle, the microbubble may collapse, thereby reducing the risk of microemboli. Further, as depicted in the embodiment of FIG. 2, different sets of surface-modified alumina particles may be disposed within multiple nitrogen gas entrapment chambers in a multiple-stage approach to chemical entrapment of nitrogen gas.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A process comprising removing air bubbles from extracorporeal blood via chemical entrapment of nitrogen ($N_2$) gas, wherein the chemical entrapment includes dinitrogen fixation by an organometallic complex.

2. The process of claim 1, wherein the organometallic complex includes a titanium (IV) complex.

3. The process of claim 1, wherein the organometallic complex is bound to a surface of an alumina particle.

4. The process of claim 3, wherein the alumina particle includes nanoparticulate alumina.

5. The process of claim 4, wherein the nanoparticulate alumina includes a powder having a surface area in a range between 60 $m^2/g$ and 70 $m^2/g$.

* * * * *